United States Patent [19]

Kaplan

[11] 4,224,237

[45] * Sep. 23, 1980

[54] CATALYTIC PROCESS FOR POLYHYDRIC ALCOHOLS AND DERIVATIVES

[75] Inventor: Leonard Kaplan, Charleston, W. Va.

[73] Assignee: Union Carbide Corporation, New York, N.Y.

[ * ] Notice: The portion of the term of this patent subsequent to Mar. 16, 1993, has been disclaimed.

[21] Appl. No.: 61,456

[22] Filed: Jul. 27, 1979

Related U.S. Application Data

[63] Continuation of Ser. No. 615,093, Sep. 19, 1975, abandoned, which is a continuation-in-part of Ser. No. 537,885, Jan. 2, 1975, abandoned.

[51] Int. Cl.$^2$ .................... C07C 27/06; C07C 29/16

[52] U.S. Cl. .................. 260/449 L; 252/431 R; 252/431 N; 252/431 P; 252/431 L; 252/443; 260/449.5

[58] Field of Search .................. 260/449 L, 449 R

[56] References Cited

U.S. PATENT DOCUMENTS 3,944,588   3/1976   Kaplan .................. 260/449 L

*Primary Examiner*—Howard T. Mars
*Attorney, Agent, or Firm*—Marylin Klosty

[57] ABSTRACT

This invention relates to the manufacture of such valuable chemicals as polyhydric alcohols, their ether and ester derivatives, oligomers of such alcohols and monohydric alcohols and their ether and ester derivatives by reacting hydrogen and oxides of carbon in the presence of a rhodium carbonyl complex dissolved in a sulfone solvent.

54 Claims, No Drawings

CATALYTIC PROCESS FOR POLYHYDRIC ALCOHOLS AND DERIVATIVES

This application is a continuation of my prior and copending application Ser. No. 615,093, filed Sept. 19, 1975 now abandoned, which in turn is a continuation-in-part of Ser. No. 537,885, filed Jan. 2, 1975, now abandoned.

This invention is concerned with the manufacture of polyhydric alcohols, their ether and ester derivatives, and oligomers of such alcohols. This invention also produces monohydric alcohols such as methanol, and their ether and ester derivatives.

It is known that monofunctional compounds such as methanol can be obtained by reaction between carbon monoxide and hydrogen at elevated pressures, e.g., up to about 1000 atmospheres, and temperatures ranging from 250° C. to 500° C., using mixtures of copper, chromium and zinc oxides as the catalyst therefor. It is disclosed in U.S. Pat. No. 2,451,333 that polyhydroxyl compounds are produced by reaction of formaldehyde, carbon monoxide, and hydrogen in the presence of hydrogenation catalysts. It has also been reported that formaldehyde can be produced by reaction between carbon monoxide and hydrogen at elevated pressures but repeated attempts to carry out this synthesis of formaldehyde have invariably failed to yield any substantial quantity of the desired product. It is generally recognized that the previously disclosed processes for the synthesis of formaldehyde from carbon monoxide and hydrogen at high pressures are either completely inoperative or else give rise to insignificantly small quantities of formaldehyde.

In British Pat. No. 655,237, published July 11, 1951, there is disclosed the reaction between carbon monoxide and hydrogen at elevated pressures and temperatures, e.g., above 1500 atmospheres at temperatures up to 400° C., using certain hydrogenation catalysts as exemplified by cobalt-containing compounds. U.S. Pat. Nos. 2,534,018; 2,570,792, and 2,636,046 are substantially similar in disclosure to the above said British patent. The only catalysts employed in the numbered examples of said U.S. Pat. No. 2,636,046 are those which contain cobalt.

It is also well-known that nickel is predominantly a catalyst for synthesis and for reforming methane according to the reaction

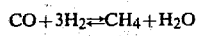

whose equilibrium favors the right hand side of the equation at temperatures below about 500° C. and the left hand side of the equation at higher temperatures; see Kirk-Othmer, Encyclopedia of Chemical Technology, Second Edition, Volume 4, pages 452-453, John Wiley and Sons, New York (1964).

Polyhydric alcohols are presently being produced synthetically by the oxidation of petroleum derived materials. Owing to the limited availability of petroleum sources, the cost of these petroleum derived materials has been steadily increasing. Many have raised the dire prediction of a significant oil shortage in the future. The consequence of this has been the recognition of the need for a new low cost source of chemicals which can be converted into such polyhydric alcohols.

This invention is directed to the process of making polyhydric aliphatic alcohols, and to their ether, ester and oligomer derivatives. In particular, this invention is concerned with the diols and triols, containing 2 or 3 carbon atoms, their ethers, ester and oligomer derivatives. A byproduct of this invention is the manufacture of the lesser valuable, but valuable nevertheless, monohydric alkanols such as methanol, ethanol and propanols, and their ether and ester derivatives. The products of the process of this invention contain carbon, hydrogen and oxygen.

There are described in U.S. Pat. No. 3,833,634, issued Sept. 3, 1974, and copending application Ser. No. 462,109, filed Apr. 18, 1974, now U.S. Pat. No. 3,957,857, issued May 18, 1976, processes for reacting hydrogen and oxides of carbon in the presence of rhodium carbonyl complex catalysts. One problem associated with these processes is preventing the loss of the catalyst during the reaction so as to avert catalyst losses. Inasmuch as the rhodium used in the catalyst is an extremely expensive metal, having a current dealer's price of about $285. per troy ounce, it is particularly desirable to avoid any significant loss of such rhodium values during the course of the reaction.

In accordance with the practice of the present invention these losses of rhodium may be significantly reduced when the aforementioned reactions of hydrogen and oxides of carbon are conducted in the presence of an organic sulfone solvent.

The process of the present invention involves the production of alkane diols and triols having from 2 to 3 carbon atoms in the molecule by reacting a mixture of hydrogen and oxides of carbon in the presence of a rhodium carbonyl complex and dimethylsulfone or a tetramethylene sulfone solvent.

A tetramethylene sulfone as used herein and as embraced by the claims shall be defined as any substituted or unsubstituted tetrahydrothiophene-1,1-dioxide, hereinafter referred to as tetramethylene sulfone or sulfolane, which when present as a solvent for the rhodium carbonyl complex catalyzed reaction of hydrogen and an oxide of carbon at a temperature of about 100° C. to about 375° C. and correlated with a pressure of from about 1000 psia to about 50,000 psia will produce a polyhydric alcohol.

Illustrative of tetramethylene sulfone solvents useable in practicing the present invention include sulfolanes of the formula:

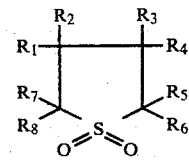

wherein each of $R_1$ through $R_8$ is at least one of hydrogen; hydroxyl; straight or branched chain alkyl, preferably having from 1 to 12 carbon atoms, most preferably 1 to 6 carbon atoms in the alkyl chain, such as methyl, ethyl, isopropyl, butyl, octyl, dodecyl and the like; a cycloaliphatic group including the monocyclic and bicyclic groups such as cyclopentyl, cyclohexyl, bicyclo [2.2.1] heptyl, and the like; or an aryl, alkyl-aryl, or aralkyl group such as phenyl, naphthyl, xylyl, tolyl, benzyl, beta-phenylethyl and the like; an ether of the formula $+O—R°)$ wherein $R°$ may be aryl or lower alkyl having from 1 to 12 carbon atoms, preferably 1 to 4 carbon atoms in the alkyl chain; an alkylene or polyalkylene ether of the formula —(OC$_n$H$_{2n}$)$_x$—OR°°
wherein n has an average value of from 1 to about 4, x
has an average value of from 1 to about 150, preferably
1 to about 20, most preferably 1 to about 4, and R°°
may be hydrogen or alkyl having from 1 to 6 carbon atoms
in the alkyl chain, such as poly(oxyethylene), poly(oxypropylene), poly(oxyethylene-oxypropylene), alkylene
and polyalkylene glycols and lower alkyl ethers thereof;
a carboxylate group of the formula:

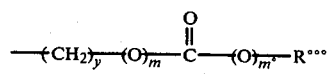

wherein y may have any value between 0 and 12, m and m° may be zero or one provided that when either m or m° is one the other is zero, and R°°° may be a lower alkyl group having from 1 to 12 carbon atoms, preferably from 1 to 4 carbon atoms, or aryl; and the like. Preferably the sulfone used in the practice of the present invention is tetrahydrothiophene-1,1-dioxide, better known as tetramethylene sulfone or sulfolane. In those instances where it may be desirable to use a substituted sulfolane those substituted in the 3 or 3,4 positions of the sulfolane ring are preferred.

The rhodium carbonyl complexes suitable for use in the practice of the present invention are those wherein the complex is at least one of (1) rhodium in complex combination with carbon monoxide, (2) rhodium in complex combination with carbon monoxide and hydrogen, (3) rhodium in complex combination with carbon monoxide and at least one Lewis base, (4) rhodium in complex combination with carbon monoxide, hydrogen and at least one Lewis base, and (5) mixtures thereof.

Morever, the rhodium carbonyl complexes of this invention may be in the form of rhodium carbonyl clusters. P. Chini, in a review article entitled "The Closed Metal Carbonyl Clusters" published in Review (1968), Inorganica Chimica Acta, pages 30-50, states that a metal cluster compound is "a finite group of metal atoms which are held together entirely, mainly or at least to a significant extent, by bonds directly between the metal atoms even though some nonmetal atoms may be associated intimately with the cluster". The rhodium carbonyl cluster compounds of this invention contain rhodium bonded to rhodium or rhodium bonded to another metal, such as cobalt, and/or iridium. The preferred rhodium carbonyl cluster compounds of this invention are those which contain rhodium-rhodium bonds. These compounds desirably contain carbon and oxygen in the form of carbonyl (—C—O), in which the carbonyl may be "terminal", "edge-bridging", and/or "face-bridging". They may also contain hydrogen and carbon in forms other than carbonyl. Illustrative structures of two distinct rhodium carbonyl clusters RH$_6$(CO)$_{16}$ and [Rh$_{12}$(CO)$_{30}$]$^{2-}$ are disclosed in U.S. Pat. No. 3,957,857.

The structures of the rhodium carbonyl clusters may be ascertained by X-ray crystal diffraction, nuclear magnetic resonance (NMR) spectra, or infrared spectra as disclosed in the article entitled "Synthesis and Properties of the Derivatives of the [Rh$_{12}$(CO)$_{30}$]$^{2-}$ Anion" by P. Chini and S. Martinengo; appearing in Inorganica Chimica Acta, 3:2 pp 299-302, June (1969). Of particular analytical utility in the present invention is the use of infrared spectroscopy which allows for characterization of the particular rhodium carbonyl complex present during the operation of the process of the present invention.

The rhodium carbonyl complex is, as characterized above, a rhodium containing compound in which the rhodium is complexed with CO. This can be achieved with just carbon monoxide or in addition to the carbon monoxide there may be included hydrogen and/or other organic or inorganic Lewis base materials to create the complex. In the last case, "complex" means a coordination compound formed by the union of one or more electronically rich molecules or atoms capable of independent existence with one or more electronically poor molecules or atoms, each of which is also capable of independent existence. The precise role of these Lewis bases in the reaction of the present invention is not fully appreciated at present. They may be functioning as ligands and/or forming counter-ions under the reaction conditions of the present process or they may be functioning just merely as Lewis bases and neutralizing or tying up a molecular species which if allowed to remain "free" or in its non-base-bound state would adversely affect the productivity of the present invention.

Organic Lewis bases which are suitable in the practice of the present invention contain at least one Lewis base oxygen atom and/or one Lewis base nitrogen atom said atoms possessing a pair of electrons available for the formation of coordinate bonds. In suitable embodiments the organic Lewis bases contain from 1 and upwards to 4 Lewis base atoms, preferably from 1 to 3 such atoms, and most preferably 1 or 2 Lewis base atoms. These organic Lewis bases are said to be multidentate or polydentate, that is to say, they are bidentate, tridentate, or quadridentate, depending on whether 2, 3 or 4 Lewis base atoms are involved.

Those organic Lewis bases which contain at least one Lewis base nitrogen atom plus at least one Lewis base oxygen atom will oftentimes hereinafter be referred to as "organic aza-oxa" Lewis bases.

Suitable organic nitrogen Lewis bases most generally contain carbon, hydrogen, and nitrogen atoms. Suitable organic oxygen Lewis bases most generally contain carbon, hydrogen, and oxygen atoms. Suitable organic aza-oxa Lewis bases most generally contain carbon, hydrogen, oxygen, and nitrogen atoms. The carbon atoms can be acyclic and/or cyclic such as aliphatic, cycloaliphatic, aromatic (including fused and bridged) carbon atoms, and the like. Preferably, the organic Lewis bases contain from 2 to 60, most preferably 2 to 40 carbon atoms. The nitrogen atoms can be in the form of imino (—N=), amino (—N—), nitrilo (N≡), etc. Desirably, the Lewis base nitrogen atoms are in the form of imino nitrogen and/or amino nitrogen. The oxygen atoms can be in the form of groups such as hydroxyl (aliphatic or phenolic),

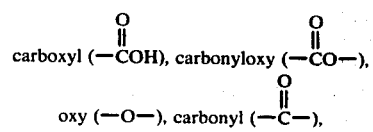

etc., all of said groups containing Lewis base oxygen atoms. In this respect, it is the "hydroxyl" oxygen in the

group and the "oxy" oxygen in the

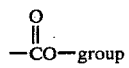

group that are acting as the Lewis base atoms. The organic Lewis bases may also contain other atoms and/or groups such as alkyl, cycloalkyl, aryl, chloro, thiaalkyl, trialkylsilyl, and the like.

Illustrative organic oxygen Lewis bases include, by way of illustrations, glycolic acid, methoxyacetic acid, ethoxyacetic acid, diglycolic acid, thiodiglycolic acid, diethyl ether, tetrahydrofuran, dioxane, tetrahydropyran, pyrocatechol, citric acid, 2-methoxyethanol, 2-ethoxyethanol, 2-n-propoxyethanol, 2-n-butylethanol, 1,2,3-trihydroxybenzene, 1,2,4-trihydroxybenzene, 2,3-dihydroxynaphthalene, cyclohexane-1,2-diol, oxetane, 1,2-dimethoxybenzene, 1,2-diethoxybenzene, methyl acetate, ethanol, 1,2-dimethoxyethane, 1,2-diethoxyethane, 1,2-di-n-propoxyethane, 1,2-di-n-butoxyethane, pentane-2,4-dione, hexane-2,4-dione, heptane-3,5-dione, octane-2,4-dione, 1-phenylbutane-1,3-dione, 3-methylpentane-2,4-dione; the mono- and dialkyl ethers of propylene glycol, of diethylene glycol, of dipropylene glycol; and the like.

Illustrative organic aza-oxa Lewis bases include, for example, the alkanolamines, such as, ethanolamine, diethanolamine, isopropanolamine, di-n-propanolamine, and the like; N,N-dimethylglycine, N,N-diethylglycine; iminodiacetic acid, N-methyliminodiacetic acid; N-methyldiethanolamine; 2-hydroxypyridine, 2,4-dihydroxypyridine, 2-methoxypyridine, 2,6-dimethoxypyridine, 2-ethoxypyridine; lower alkyl substituted hydroxypyridines, such as 4-methyl-2-hydroxypyridine, 4-methyl-2,6-dihydroxypyridine, and the like; morpholine, substituted morpholines, such as 4-methylmorpholine, 4-phenylmorpholine; picolinic acid, methyl-substituted picolinic acid; nitrilotriacetic acid, 2,5-dicarboxypiperazine, N-(2-hydroxyethyl) iminodiacetic acid, ethylenediaminetetraacetic acid; 2,6-dicarboxypyridine; 8-hydroxyquinoline, 2-carboxyquinoline, cyclohexane-1,2-diamine-N,N,N',N'-tetraacetic acid, the tetramethyl ester of ethylenediamine-tetraacetic acid, and the like.

Illustrative of the Lewis base nitrogen containing compounds suitable for use in the practice of the present invention are ammonia and the amines. Any primary, secondary, or tertiary amine is suitable in the practice of the present invention. This includes the mono-, di-, tri-, and polyamines and those compounds in which the Lewis base nitrogen forms part of a ring structure as in pyridine, quinoline, pyrimidine, morpholine, hexamethylene tetraamine, and the like. In addition any compound capable of yielding an amino nitrogen under the reaction conditions of the present invention is suitable, as in the case of an amide, such as formamide and urea, or an oxime. Further illustrative of these Lewis base nitrogen compounds are ammonia; aliphatic amines such as methylamine, ethylamine, n-propylamine, isopropylamine, octylamine, dodecylamine, dimethylamine, diethylamine, diisoamylamine, methylethylamine, diisobutylamine, trimethylamine, methyldiethylamine, triisobutylamine, tridecylamine, and the like; aliphatic and aromatic di- and polyamides such as 1,2-ethanediamine, 1,3-propanediamine, N,N,N',N'-tetramethylenediamine, N,N,N',N'-tetraethylethylenediamine, N,N,N',N'-tetra-n-propylethylenediamine, N,N,N',N'-tetrabutylenediamine, o-phenylenediamine, m-phenylenediamine, p-phenylenediamine, p-tolylenediamine, o-tolidene, N,N,N',N'-tetramethyl-p-phenylenediamine, N,N,N',N'-tetraethyl-4,4'-biphenyldiamine, and the like; aromatic amines such as aniline, 1-naphthylamine, 2-naphthylamine, p-toluidine, o-3-xylidine, p-2-xylidine, benzylamine, diphenylamine, dimethylaniline, diethylaniline, N-phenyl-1-naphthylamine, bis-(1,8)-dimethylaminonaphthalene, and the like; alicyclic amines such as cyclohexylamine, dicyclohexylamine, and the like; heterocyclic amines such as piperidine; substituted piperidines such as 2-methylpiperidine, 3-methylpiperidine, 4-ethylpiperidine, and 3-phenylpiperidine; pyridine; substituted pyridines such as 2-methylpyridine, 2-phenylpyridine, 2-methyl-4-ethylpyridine, 2,4,6-trimethylpyridine, 2-dodecylpyridine, 2-chloropyridine, and 2-(dimethylamino)pyridine; quinoline; substituted quinolines, such as 2-(dimethylamino)-6-methoxyquinoline; 4,5-phenanthroline; 1,8-phenanthroline; 1,5-phenanthroline; piperazine; substituted piperazines such as N-methylpiperazine, N-ethylpiperazine, 2,N-dimethylpiperazine; 2,2'-dipyridyl, methyl-substituted 2,2'-dipyridyl; ethyl-substituted 2,2'-dipyridyl; 4-triethylsilyl-2,2'-dipyridyl; 1,4-diazabicyclo[2.2.2]octane methyl substituted 1,4-diazabicyclo[2.2.2]octane, purine and the like.

Illustrative of the inorganic Lewis bases useful in the practice of the present invention are ammonia, hydroxides and halides, such as chloride, bromide, iodide, or fluoride; or mixtures thereof.

Any of the above Lewis bases may be provided to the reaction in compound form or as ligands which are in complex combination with the rhodium carbonyl compound initially charged to the reactor.

The precise role of the rhodium carbonyl complexes, such as the rhodium carbonyl clusters characterized previously, in the reaction of hydrogen with oxides of carbon to produce polyhydric alcohols is not fully appreciated at present. Under the reaction conditions of the present process the carbonyl complexes are believed to be anionic in their active forms. Rhodium carbonyl anions are known to be involved in the following set of reactions as indicated by S. Martinengo and P. Chini, in Gazz. Chim. Ital., 102, 344 (1972) and the references cited therein.

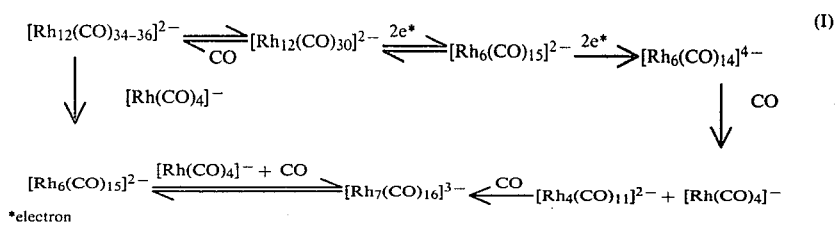

*electron

Infrared spectra under reaction conditions of the present process have shown both the $Rh(CO)_4^-$ and $[Rh_{12}(CO)_{34-36}]^{2-}$ anions to be present at various concentrations at different times of the reaction. Therefore the set of reactions and equilibria shown in I above may represent the active rhodium carbonyl species responsible for polyhydric alcohol formation or may be merely symptomatic of some further intermediate transitory rhodium carbonyl structure which serves to convert the carbon monoxide and hydrogen to the polyhydric alcohol.

Assuming the active catalytic species is a rhodium carbonyl complex anion, or the formation of the active species under reaction conditions is directly dependent on the existence of these anions, allows one to better explain, in terms of reaction rates, productivity and catalyst stability, the role the sulfone solvents, particularly the tetramethylene sulfones, play in the reaction whereby hydrogen and an oxide of carbon are converted to the polyhydric alcohol. It is believed that the sulfones enhance the reactivity of these rhodium carbonyl complex anions because a "naked", reactive anion is produced. Naked rhodium carbonyl anions are believed to be produced under the reaction conditions of the present process because the sulfone solvent decreases any tendency of the rhodium carbonyl anions to ion pair, the rhodium carbonyl anions are not strongly solvated, nor is the rhodium strongly complexed by the solvent all of which tend to produce an anion having a higher degree of reactivity under the reaction conditions employed.

The novel process is suitably effected over a wide superatmospheric pressure range of from about 800 psia to about 50,000 psia. Pressures as high as 50,000 psia, and higher can be employed but with no apparent advantages attendant thereto which offset the unattractive plant investment outlay required for such high pressure equipment.

In one embodiment of this invention the upper pressure limitation is approximately 12,000 psia. Effecting the present process below about 12,000 psia, especially below about 8000 psia, and preferably at pressures below about 6000 psia, results in cost advantages which are associated with low pressure equipment requirements. However, when practicing the present invention at pressures below about 12,000 psia, the rate of desired product formation is quite slow and in order to obtain a faster reaction rate and/or higher conversions to the desired product there is provided to the reaction a promoter which may be a salt and/or an organic Lewis base nitrogen compound. In those instances where the Lewis base nitrogen compound is contained as a ligand in the rhodium carbonyl complex charged to the reactor or where anion of the salt promoter charged to the reactor is a rhodium carbonyl complex such as cesium triacontacarbonylrhodate, it may not be necessary to add to the reaction any additional amounts of these promoters. A suitable pressure range for effecting the reaction in the presence of these promoters is from about 1000 psia to about 12,000 psia, preferably from about 4000 to about 12,000 psia.

In a preferred embodiment of the present invention the pressures referred to above represent the total pressures of hydrogen and oxides of carbon in the reactor.

Suitable salts useful in the practice of the present invention at pressures below about 12,000 psia include any organic or inorganic salt which does not adversely affect the production of polyhydric alcohols. Experimental work completed to data indicates that any salt will show this promoter effect under some, but not all, glycol-producing conditions. Illustrative of the salts useful in the practice of the present invention are the ammonium salts and the salts of the metals of Group I and Group II of the Periodic Table (Handbook of Chemistry and Physics—50th Edition) for instance the halide, hydroxide, alkoxide, phenoxide and carboxylate salts such as sodium fluoride, cesium fluoride, cesium pyridinolate, cesium formate, cesium acetate, cesium benzoate, cesium p-methylsulfonyl benzoate $(CH_3SO_2C_6H_4COO)Cs$, rubidium acetate, magnesium acetate, strontium acetate, ammonium formate, ammonium benzoate and the like. Preferred are the cesium and ammonium carboxylate salts, most preferably their formate, benzoate and para-lower alkyl sulfonyl benzoate salts.

Also useful in the practice of the present invention are organic salts of the following formula:

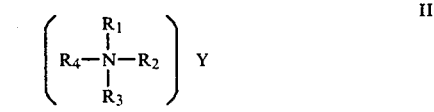

quaternary ammonium salts

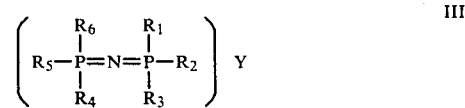

bis(triorgano phosphine)iminium salts wherein $R_1$ through $R_6$ in formulas (II) and (III) above are any organic radicals which do not adversely affect the production of polyhydric alcohols by reacting oxides of carbon with hydrogen in the presence of the aforedefined rhodium carbonyl complex, such as a straight or branched chain alkyl group, having from 1 to 20 carbon atoms in the alkyl chain, such as methyl, ethyl, n-propyl, isopropyl, n-butyl, octyl, 2-ethylhexyl, dodecyl, and the like; or a cycloaliphatic group including the monocyclic and bicyclic groups cyclopentyl, cyclohexyl, and bicyclo[2.2.1]heptyl groups, and the like or an aryl, alkylaryl, or aralkyl group such as phenyl, naphthyl, xylyl, tolyl, t-butylphenyl, benzyl, beta-phenylethyl, 3-phenylpropyl and the like; or a functionally substituted alkyl such as beta-hydroxyethyl, ethoxymethyl, ethoxyethyl, phenoxyethyl, and the like; or a polyalkylene ether group of the formula $-(C_nH_{2n}O)_x-OR$ wherein n has an average value from 1 to 4, x has an average value from 2 to about 150, and R may be hydrogen or alkyl of 1 to about 12 carbon atoms. Illustrative of such polyalkylene ether groups are poly(oxyethylene), poly(oxypropylene), poly(oxyethyleneoxypropylene), poly(oxyethyleneoxybutylene), and the like. Y in formulas II and III above may be any anion which does not adversely affect the production of polyhydric alcohols in the practice of the present invention such as hydroxide; a halide, for instance fluoride, chloride, bromide and iodide; a carboxylate group, such as formate, acetate, propionate, and benzoate and the like; an alkoxide group such as methoxide, ethoxide, phenoxide, and the like; a functionally substituted alkoxide or phenoxide group such as methoxyethoxide, ethoxyethoxide, phenoxyethoxide and the like; a pyridinolate or quinolate group; and others. Preferably Y in formulas II and III, above, is a carboxylate, most preferably formate, acetate and benzoate.

A suitable method for preparing the bis(triorgano phosphine)iminium salts is disclosed in an article by Appel, R. and Hanas, A. appearing in Z. Anorg. u. Allg. Chem., 311, 290, (1961).

Other organic salts useful in the practice of the present invention include the quaternized heterocyclic amine salts such as the pyridinium, piperidinium, morpholinium, quinolinium salts and the like, e.g., N-ethylpyridinium fluoride, N-methylmorpholiniumbenzoate, N-phenylpiperidinium hydroxide, N,N'-dimethyl-2,2-bipyridinium acetate, and the like.

In one of the embodiments of the present invention, the anion of the above salt promoters may be any of the rhodium carbonyl anions. Suitable rhodium carbonyl anions include $[Rh_6(CO)_{15}]^{2-}$; $[Rh_6(CO)_{15}Y]^-$ wherein Y may be halogen, such as chlorine, bromine, or iodine, $[Rh_6(CO)_{15}(COOR'')]^-$ wherein R'' is lower alkyl or aryl such as methyl, ethyl, or phenyl; $[Rh_6(CO)_{14}]^{2-}$; $[Rh_7(CO)_{16}]^{3-}$; and $[Rh_{12}(CO)_{30}]^{2-}$.

Under reaction conditions where a salt promoter is employed the salt is desirably added with the initial charge of reactants in amounts of from about 0.5 to about 2.0 moles, preferably from about 0.8 to about 1.6 moles, and most preferably from about 0.9 to 1.4 moles of salt for every five atoms of rhodium present in the reaction mixture.

The Lewis base nitrogen promoters may be any of the Lewis base nitrogen or organic aza-oxa Lewis base compounds defined above. Preferably the Lewis base nitrogen promoters are amines. This also includes those compounds where the nitrogen is part of a heterocyclic ring such as the pyridines, pyrimidines, piperidines, morpholines, quinolines and the like. Illustrative of these preferred Lewis base promoters are pyridine, 2,4,6-trimethylpyridine, 4-dimethylaminopyridine, 4-tridecylpyridine, isobutylamine, triethylamine, N-methylpiperidine, N-methylmorpholine, bis-(1,8)-dimethylaminonaphthalene, 1,4-diazabicyclo[2.2.2]-octane, and quinuclidine.

Under reaction conditions where a Lewis base nitrogen compound is used as a promoter it is preferably used in amounts from about 0.02 to about 2 equivalents of promoter, most preferably from about 0.1 to about 1 equivalent of promoter, for every mole of rhodium in the reaction mixture. The number of equivalents of promoter is equal to the number of moles of promoter times the number of nitrogen atoms in each molecule.

Mixtures of the above salt and amine low pressure promoters may be used in the practice of the present invention.

The salt and/or Lewis base nitrogen low pressure promoters may be added to the reaction in compound form or there may be added to the reactor any substance capable of generating the salt and/or the amine promoter in situ either prior to or during the reaction conditions of the present invention.

For instance an amide such as formamide, urea, and the like or an oxime may be added to the reactor in place of the amine promoter.

Another and preferred group of low pressure promoters include the trialkanolamine borates, preferably those having the formula:

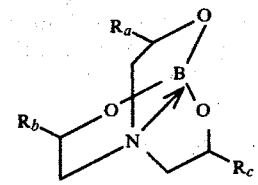

wherein $R_a$, $R_b$, and $R_c$ may be at least one of hydrogen or lower alkyl having from 1 to 12 carbon atoms in the alkyl chain. Most preferably the trialkanolamine borates useful in the practice of the present invention are triethanolamine borate and triisopropanolamine borate.

The sulfones useful in the practice of the present invention may be used in admixture with other conventional miscible solvents, preferably wherein the solvent mixtures contain the sulfone in amounts of from about 25 to 99, most preferably from about 50 to about 99 percent by weight of the total solvent mixture.

Illustrative of solvents which may be used in admixture with the sulfone are the alkanols such as methanol, ethanol, propanol, 2-ethylhexanol and the like; esters such as methyl acetate, propyl acetate, butyl acetate and the like; lactones such as gamma-butyrolactone, delta-valerolactone, and the like; ethers such as tetrahydrofuran, tetrahydropyran, dimethyl ether, diethyl ether, 1,2-diethoxybenzene, the mono- and dialkyl ethers of alkylene and polyalkylene glycols, such as the mono- and dimethyl and ethyl ethers of ethylene glycol, propylene glycol, butylene glycol, diethylene glycol, dipropylene glycol, triethylene glycol, tetraethylene glycol, dipropylene glycol, oxyethylene-oxypropylene glycol and the like; and water.

The quantity of catalyst employed is not narrowly critical and can vary over a wide range. In general, the novel process is desirably conducted in the presence of a catalytically effective quantity of the active rhodium species which gives a suitable and reasonable reaction rate. Reaction proceeds when employing as little as about $1 \times 10^{-6}$ weight percent, and even lesser amounts, of rhodium metal based on the total weight of reaction mixture. The upper concentration limit can be quite high, e.g., about thirty weight percent rhodium, and higher, and the realistic upper limit in practicing the invention appears to be dictated and controlled more by economics in view of the exceedingly high cost of rhodium metal and rhodium compounds. Depending on various factors such as the promoter of choice, the partial pressures of hydrogen and oxides of carbon, the total operative pressure of the system, the operative temperature, the choice of the organic co-diluent, and other considerations, a catalyst concentration of from about $1 \times 10^{-5}$ to about 5 weight percent rhodium (contained in the complex catalyst) based on the total weight of reaction mixture, is generally desirable to the practice of the invention.

The operative temperature which may be employed can vary over a wide range of elevated temperatures. In general, the novel process can be conducted at a temperature in the range of from about 100° C. and upwards to approximately 375° C., and higher. Operative temperatures outside this stated range, though not excluded from the scope of the invention, do not fall within certain desirable embodiments of the invention. At the lower end of the temperature range, and lower, the rate of reaction to desired product becomes markedly slow. At the upper temperature range, and beyond, signs of some catalyst instability are noted. Notwithstanding this factor, reaction continues and polyhydric alcohols and/or their derivatives are produced. Additionally, one should take notice of the equilibrium reaction for forming ethylene glycol:

$$2CO + 3H_2 \rightleftharpoons HOCH_2CH_2OH$$

At relatively high temperatures the equilibrium increasingly favors the left hand side of the equation. To drive the reaction to the formation of increased quantitites of ethylene glycol, higher partial pressures of carbon monoxide and hydrogen are required. Processes based on correspondingly higher operative pressures, however, do not represent preferred embodiments of the invention in view of the high investment costs associated with erecting chemical plants which utilize high pressure utilities and the necessity of fabricating equipment capable of withstanding such enormous pressures. Suitable operative temperatures are between about 150° C. to about 300° C., and desirably from about 190° C. to about 275° C.

The novel process is effected for a period of time sufficient to produce the desired polyfunctional oxygen-containing products and/or derivatives thereof. In general, the residence time can vary from minutes to several hours, e.g., from a few minutes to approximately 24 hours, and longer. It is readily appreciated that the residence period will be influenced to a significant extent by the reaction temperature, the concentration and choice of the catalyst, the total gas pressure and the partial pressure exerted by its components, the concentration, and other factors. The synthesis of the desired product(s) by the reaction of hydrogen with an oxide of carbon is suitably conducted under operative conditions which give reasonable reaction rates.

The relative amounts of oxide of carbon and hydrogen which are initially present in the reaction mixture can be varied over a wide range. In general, the mole ratio of $CO:H_2$ is in the range of from about 20:1 to about 1:20, suitably from about 10:1 to about 1:10, and preferably from about 5:1 to about 1:5.

It is to be understood, however, that molar ratios outside the aforestated broad range may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention. For instance, polyhydric alcohols are obtained by using mixtures containing carbon dioxide and hydrogen. Mixtures of carbon dioxide, carbon monoxide and hydrogen can also be employed. If desired, the reaction mixture can comprise steam and carbon monoxide.

The novel process can be executed in a batch, semi-continuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be fitted with internal and/or external heat exchanger(s) to thus control undue temperature fluctuations, or to prevent any possible "runaway" reaction temperatures due to the exothermic nature of the reaction. In preferred embodiments of the invention, agitation means to vary the degree of mixing of the reaction mixture can be suitably employed. Mixing induced by vibration, shaker, stirrer, rotatory, oscillation, ultrasonic, etc., are all illustrative of the types of agitation means which are contemplated. Such means are available and well-known to the art. The catalyst may be initially introduced into the reaction zone batchwise, or it may be continuously or intermittently introduced into such zone during the course of the synthesis reaction. Means to introduce and/or adjust the reactants, either intermittently or continuously, into the reaction zone during the course of the reaction can be conveniently utilized in the novel process especially to maintain the desired molar ratios of and the partial pressures exerted by the reactants.

As intimated previously, the operative conditions can be adjusted to optimize the conversion of the desired product and/or the economics of the novel process. In a continuous process, for instance, when it is preferred to operate at relatively low conversions, it is generally desirable to recirculate unreacted synthesis gas with-/without make-up carbon monoxide and hydrogen to the reaction. Recovery of the desired product can be achieved by methods well-known in the art such as by distillation, fractionation, extraction, and the like. A fraction comprising rhodium catalyst, generally contained in byproducts and/or normally liquid organic diluent, can be recycled to the reaction zone, if desired. All or a portion of such fraction can be removed for recovery of the rhodium values or regeneration to the active catalyst can be intermittently added to the recycle stream or directly to the reaction zone.

The active forms of the rhodium carbonyl clusters may be prepared by various techniques. They can be preformed and then introduced into the reaction zone. Alternatively, any of the host of rhodium-containing substances as well as any of the low pressures promoters can be introduced into the reaction zone and, under the operative conditions of the process (which of course includes hydrogen and carbon monoxide), the active rhodium carbonyl cluster can be generated in situ. Illustrative of rhodium-containing substances which can be conveniently introduced or placed in the synthesis zone include, for example, rhodium oxide ($Rh_2O_3$), tetrarhodium dodecacarbonyl, dirhodium octacarbonyl, hexarhodium hexadecacarbonyl ($Rh_6(CO)_{16}$), rhodium(II)

formate, rhodium(II) acetate, rhodium(II) propionate, rhodium(II) butyrate, rhodium(II) valerate, rhodium(III) naphthenate, rhodium dicarbonyl acetylacetonate, rhodium tri(acetylacetonate), rhodium trihydroxide, indenyl-rhodium dicarbonyl, rhodium dicarbonyl (1-phenylbutane-1,3-dione), tri(hexane-2,4-dionato)rhodium(III), tris(heptane-2,4-dionato)rhodium(III), tris(1-phenylbutane-1,3-dionato)rhodium(III), tris(3-methylpentane-2,4-dionato)rhodium(III), tris(1-cyclohexylbutane-1,3-dionato)rhodium(III), triacontacarbonyl rhodium salts and rhodium-containing compounds deposited on porous supports or carriers capable of providing rhodium carbonyls in solution, and others.

The preparation of the rhodium carbonyl complex compounds can be conveniently carried out in the sulfone solvent, the co-diluent or mixtures thereof. Tetrarhodium dodecacarbonyl, though of limited solubility, can be added to the solvent in a finely divided form. Any of several of the rhodium-containing compounds illustrated previously can be employed in lieu of tetrarhodium dodecacarbonyl. The organic Lewis bases such as pyridine, or other promoters, such as the aforedefined low pressure salt promoters, can also be added thereto. The rhodium carbonyl complex or cluster forming reaction can be effected under a carbon monoxide pressure, with or without $H_2$, of about 1 to 15 atmospheres, and higher, using a temperature of about 30° C. to about 100° C., for a period of time ranging from minutes to a few days, generally from about 30 minutes to about 24 hours. The resulting rhodium carbonyl complex contained in the sulfone solvent is catalytically active in this process. In preparing the aforesaid complexes, one can suitably employ from about 0.01 to about 25 moles salt or Lewis base nitrogen promoters per mole of rhodium (contained in the rhodium compound used as a rhodium source). Ratios outside this stated range can be employed especially when it is desirable to use diluent quantities of the low pressure promoters.

The equipment arrangement and procedure which provides the capability for determining the existence of anionic rhodium carbonyl complexes or clusters having defined infrared spectrum characteristics, during the course of the manufacture of polyhydric alcohols from carbon monoxide and hydrogen, pursuant to this invention is disclosed and schematically depicted in U.S. patent application Ser. No. 462,109, filed Apr. 18, 1974, now U.S. Pat. No. 3,957,857, issued May 18, 1976, the disclosure of which is incorporated herein by reference.

A particularly desirable infrared cell constructure is described in copending U.S. patent application, Ser. No. 451,437, filed Mar. 15, 1974, now U.S. Pat. No. 3,886,364, issued May 27, 1975, and its disclosure of a preferred cell construction is incorporated herein by reference.

The "oxide of carbon" as covered by the claims and as used herein is intended to mean carbon monoxide and mixtures of carbon dioxide and carbon monoxide, either introduced as such or formed in the reaction. Preferably the oxide of carbon is carbon monoxide.

The reaction of the present invention is conducted in what is believed to be a homogeneous liquid phase, which means that the catalyst, the reaction products and the promoter if present are in solution. Though the reaction to produce alcohols is essentially homogeneous, there may be small amounts of insoluble catalyst particles depending on the reaction conditions employed.

The following examples are merely illustrative and are not presented as a definition of the limits of the invention.

The sulfolane used in the following examples was purified prior to use according to the method disclosed by E. N. Arnett and C. F. Douty, reported in the Journal of the American Chemical Society, 86, 409 (1964).

The 3,4-bis(2-methoxyethoxy) sulfolane used in the following examples was prepared by reacting the monomethylether of ethylene glycol with 3,4-dichlorosulfolane using a sodium hydroxide catalyst at atmospheric pressure and temperature of 20°–25° C. for 4 hours and 40°–50° C. for 1 hour. The refined product had a boiling point of 153°–154° C. at 0.25 mm of Hg and a purity of 99.8 percent.

Other materials used in the following examples possessed the following characteristics: cesium benzoate (recrystallized from $H_2O$ Analysis Found: C, 32.62; H, 1.90. Calcd. for $C_7H_5O_2Cs$: C, 33.10; H, 1.98). Ammonium acetate and ammonium benzoate were purchased from PCR, Inc., Gainesville, Fla. (veripur grade). Triisopropanolamine borate (mp. 155°–157.5°).

EXAMPLE 1

A 150 ml. capacity stainless steel reactor capable of withstanding pressures up to 7,000 atmospheres was charged with a premix of 75 cubic centimeters (cc) of sulfolane, 3.0 millimoles (mmol), 0.77 grams, of rhodium dicarbonylacetylacetonate, and 0.625 mmol of pyridine. The reactor was sealed and charged with a gaseous mixture, containing equal molar amounts of carbon monoxide and hydrogen, to a pressure of 8,000 pounds per square inch (psig). Heat was applied to the reactor and its contents; when the temperature of the mixture inside the reactor reached 190° C., as measured by a suitably placed thermocouple, an additional adjustment of carbon monoxide and hydrogen ($H_2$:CO=1:1 mole ratio) was made to bring the pressure back to 8000 psig. The temperature was maintained at 240° C. for 4 hours. During this period of time additional carbon monoxide and hydrogen was added whenever the pressure inside the reactor dropped below about 7500 psig. With these added repressurizations the pressure inside the reactor was maintained at 8000 psig ±400 psig over the entire 4 hour period.

After the 4 hour period, the vessel and its contents were cooled to room temperature, the excess gas vented and the reaction product mixture was removed. Analysis of the reaction product mixture was made by gas chromatographic analysis using a Hewlett Packard FM ™ model 810 Research Chromatograph.

Analysis of the product mixture showed 5.7 grams of ethylene glycol, 2.6 grams of methanol, 0.34 grams of glycol monoformate and a rhodium recovery of 84 percent (82% +2% in wash) based on the total rhodium charged to the reactor.

Rhodium recovery was determined by atomic absorption analysis of the contents of the reactor after the venting of the unreacted gases at the end of the reaction. A further analysis was run on a "wash" of the reactor and the results of the two analyses were combined and reported as the rhodium recovered. The wash of the reactor consisted of charging to the reactor 100 cc of the solvent used for that experiment, and bringing the reactor and its contents to a temperature of 160° C. and a pressure of 14,000 to 15,000 psig and maintaining these conditions for a period of 30 minutes. The reactor was then cooled and the unreacted gases vented and an atomic absorption analysis for rhodium was run on the reactor's contents. The rhodium recovery values therefore would be the percent rhodium based on the total rhodium charged to the reactor that is soluble or suspended in the reaction mixture and the wash after the specified reaction time.

EXAMPLE 2

Example 1 was repeated except dimethyl sulfone was used as the solvent in place of sulfolane. Analysis of the product mixture showed 4.9 grams of ethylene glycol, 1.4 grams of methanol, and 0.1 grams of ethylene glycol monoformate. The amount of methanol reported represents a lower limit in that much of the methanol was probably lost when the reaction mixture was dumped at high temperature.

EXAMPLE 3

Example 1 was repeated except that 0.75 mmol. of bis-triphenylphosphine iminium acetate was used in place of the pyridine. Analysis of the product mixture showed 5.2 grams of ethylene glycol, 3.2 grams of methanol, 0.1 grams of methyl formate, 0.03 grams of ethanol 0.1 grams of ethylene glycol monoformate and a rhodium recovery of 83 percent (79%+4% from wash).

EXAMPLE 4

Example 3 was repeated except 3,4-bis(2-methoxy)ethoxy)sulfolane,

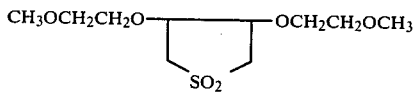

was used as the solvent in place of the sulfolane. Analysis of the product mixture showed 5.2 grams of ethylene glycol, 2.2 grams of methanol, and a rhodium recovery of 88 percent (78%+10% from wash).

EXAMPLE 5

Example 3 was repeated except dimethyl sulfone was used as the solvent in place of sulfolane. Analysis of the product mixture showed 2.2 grams of ethylene glycol and approximately 0.9 grams of methanol. (A lower limit for methanol produced as in example 2)

EXAMPLE 6

Example 1 was repeated except the promoter charge consisted of 1.25 mmol of pyridine and 0.65 mmol of cesium formate and the reaction temperature was 220° C. Analysis of the product mixture showed 1.5 grams of ethylene glycol, 2.9 grams of methanol, 0.19 grams of methyl formate and a rhodium recovery of 98 percent (91%+7% from wash).

EXAMPLE 7

Example 6 was repeated except 3,4-bis(2-methoxy)ethoxy)-sulfolane was the solvent in place of sulfolane. Analysis of the product mixture showed 2.7 grams of ethylene glycol, 2.4 grams of methanol and a rhodium recovery of 95 percent (86%+9% from wash).

EXAMPLE 8

Example 1 was repeated except the pyridine concentration was increased to 1.25 mmol. Analysis of the reaction product showed 5.0 grams of ethylene glycol, 4.4 grams of methanol, 0.53 grams of methyl formate, 0.12 grams of propylene glycol, 0.26 grams of ethylene glycol monoformate and a rhodium recovery of 85 percent (80%+5% from wash).

EXAMPLE 9

Example 8 was repeated except the reaction pressure was 6,000 psia. (pH$_2$/pCO=1/1 molar ratio) Analysis of the product mixture showed 2.2 grams of ethylene glycol, 2.4 grams of methanol, 0.15 grams of methyl formate, 0.08 grams of propylene glycol, 0.04 grams of ethylene glycol monoformate, 0.03 grams ethanol and a rhodium recovery of 81 percent (78%+3% from wash).

EXAMPLE 10

Example 9 was repeated except the reaction pressure was 12,000 psia (pCO/pH$_2$=1/1 molar ratio). Analysis of the reaction product showed 11.7 grams of ethylene glycol, 10.6 grams of methanol, 2.10 grams of methyl formate, 0.66 grams of ethylene glycol monoformate, 0.16 grams of ethanol and a rhodium recovery of 86 percent (82%+4% from wash).

EXAMPLE 11

Example 10 was repeated except the reaction pressure was 10,000 psig (partial pressure of CO=6,000 psig and partial pressure of H$_2$=4,000 psig). Analysis of the reaction product showed 8.25 grams of ethylene glycol, 7.20 grams of methanol, 1.12 grams methyl formate, 0.42 grams ethylene glycol monoformate, 0.11 grams of ethanol, and a rhodium recovery of 97 percent (93%+4% from wash).

EXAMPLE 12

Example 11 was repeated except the reaction pressure was 10,0000 psig (partial pressure of CO=5,000 psig and partial pressure H$_2$=5,000 psig). Analysis of the reaction product showed 9.2 grams of ethylene glycol, 8.0 grams of methanol, 1.1 grams of methanol formate, 0.08 grams of ethanol, 0.33 grams of ethylene glycol monoformate and a rhodium recovery of 86 percent (81%+5% from wash).

EXAMPLE 13

Example 8 was repeated except 1.25 mmol of 2-hydroxypyridine was used in place of pyridine. Analysis of the reaction mixture showed 2.7 grams of ethylene glycol, 3.8 grams of methanol and a rhodium recovery of 67 percent (61%+6% from wash).

EXAMPLE 14

Example 13 was repeated except N,N'-dimethylaniline was used in place of 2-hydroxypyridine. Analysis of the reaction product showed 1.4 grams of ethylene glycol, 4.1 grams of methanol and a rhodium recovery of 61 percent (58%+3% from wash).

EXAMPLE 15

Example 14 was repeated except 8-hydroxyquinoline was used in place of the N,N'-dimethylaniline. Analysis of the reaction product showed 3.0 grams of ethyleneglycol, 3.6 grams of methanol and a rhodium recovery of 74 percent (67%+7% from wash).

EXAMPLE 16

Example 15 was repeated except bis-(1,8)-dimethylaminonaphthalene was used in place of the 8-hydroxyquinoline. Analysis of the reaction product showed 6.0 grams of ethylene glycol, 2.9 grams of methanol and a rhodium recovery of 81 percent (78%+3% from wash).

EXAMPLE 17

Example 16 was repeated except N-methylmorpholine was used in place of the 1,8-dimethylaminonaphthalene. Analysis of the reaction product showed 5.8 grams of ethylene glycol, 3.2 grams of methanol and a rhodium recovery of 68 percent (64%+4% from wash.

EXAMPLE 18

Example 17 was repeated except 0.75 mmol of bis(triphenylphosphine)iminium acetate was added in addition to the N-methylmorpholine. Analysis of the reaction product showed 6.4 grams of ethylene glycol, 3.8 grams of methanol and a rhodium recovery of 88 percent (82%+6% from wash).

EXAMPLE 19

Example 1 was repeated except 1.30 mmol of 4-phenylpyridine was used in place of pyridine, a reaction temperature of 258° C. and 5.34 mmol of rhodium dicarbonylacetylacetonate were used. Analysis of the product mixture showed 6.7 grams of ethylene glycol, 5.4 grams of methanol and a rhodium recovery of 62 percent (59%+3% from wash).

EXAMPLE 20

Example 1 was repeated except 1.25 mmol of 4-tridecylpyridine was used in place of the pyridine. Analysis of the reaction product showed 5.2 grams of ethylene glycol, 3.8 grams of methanol and a rhodium recovery of 81 percent (78%+3% from wash).

EXAMPLE 21

Example 1 was repeated except 1,4-diazabicyclo[2.2.2]octane was used in place of pyridine and the reaction temperature was 220° C. Analysis of the reaction product showed 3.5 grams of ethylene glycol, 1.3 grams of methanol and a rhodium recovery of 88 percent (81%+7% from wash).

EXAMPLE 22

Example 21 was repeated except 0.31 mmol. of the 1,4-diazabicyclo[2.2.2]octane was used. Analysis of the reaction product showed 0.9 grams of ethylene glycol, 1.4 grams of methanol and a rhodium recovery of 74 percent (71%+3% from wash).

EXAMPLE 23

Example 22 was repeated except 1.25 mmol. of 1,4-diazabicyclo[2.2.2]octane was used. Analysis of the reaction product showed 2.6 grams of ethylene glycol, 2.8 grams of methanol and a rhodium recovery of 93 percent (87%+6% from wash).

EXAMPLE 24

Example 23 was repeated except 2.50 mmol of 1,4-diazabicyclo[2.2.2]octane was used. Analysis of the reaction product showed 1.5 grams of ethylene glycol, 2.8 grams of methanol and a rhodium recovery of 93 percent (90%+3% from wash).

EXAMPLE 25

Example 1 was repeated except 3,5-dichloropyridine was used in place of pyridine and the reaction temperature was 220° C. Analysis of the product mixture showed 1.0 grams of ethylene glycol, 0.9 grams of methanol and a rhodium recovery of 82 percent (76%+6% from wash).

EXAMPLE 26

Example 25 was repeated except pyridine was used in place of the 3,5-dichloropyridine. Analysis of the reaction product showed 3.8 grams of ethylene glycol, 2.2 grams of methanol and a rhodium recovery of 99 percent (91%+8% from wash).

EXAMPLE 27

Example 26 was repeated except 0.31 mmol of pyridine was used. Analysis of the reaction product showed 0.5 grams of ethylene glycol, 1.9 grams of methanol and a rhodium recovery of 72 percent (66%+6% from wash).

EXAMPLE 28

Example 27 was repeated except 1.25 mmol of pyridine was used. Analysis of the reaction product showed 2.1 grams of ethylene glycol, 3.3 grams of methanol and a rhodium recovery of 94 percent (87%+7% from wash).

EXAMPLE 29

Example 28 was repeated except 2.50 mmol of pyridine was used. Analysis of the reaction product showed 1.2 grams of ethylene glycol and 3.4 grams of methanol and a rhodium recovery of 104 percent (97%+7% from wash).

EXAMPLE 30

Example 1 was repeated except 0.5 mmol of cesium formate was used in place of the pyridine. Analysis of the reaction product showed 1.5 grams of ethylene glycol, 4.1 grams of methanol and a rhodium recovery of 77 percent (72%+5% from wash).

EXAMPLE 31

Example 30 was repeated except 0.65 mmol of cesium formate was used. Analysis of the reaction product showed 3.6 grams of ethylene glycol, 3.8 grams of methanol and a rhodium recovery of 86 percent (80%+6% from wash).

EXAMPLE 32

Example 30 was repeated except 0.75 mmol of cesium formate was used. Analysis of the reaction product showed 3.3 grams of ethylene glycol, 3.5 grams of methanol and a rhodium recovery of 75 percent (72%+3% from wash).

EXAMPLE 33

Example 31 was repeated except 1.0 mmol of cesium formate was used. Analysis of the reaction product showed 3.0 grams of ethylene glycol, 4.1 grams of methanol and a rhodium recovery of 84 percent (77%+7% from wash).

EXAMPLE 34

Example 33 was repeated except 0.65 mmol of cesium benzoate was used instead of the cesium formate. Analysis of the reaction product showed 4.2 grams of ethylene glycol, 3.0 grams of methanol and a rhodium recovery of 80 percent (74%+6% from wash).

EXAMPLE 35

Example 34 was repeated except 0.65 mmol of cesium isobutyrate was used instead of the cesium benzoate. Analysis of the reaction product showed 3.8 grams of ethylene glycol, 3.2 grams of methanol and a rhodium recovery of 88 percent (82%+6% from wash).

EXAMPLE 36

Example 35 was repeated except 0.65 mmol of cesium fluoride was used instead of the cesium isobutyrate. Analysis of the reaction product showed 1.9 grams of ethylene glycol, 2.5 grams of methanol and a rhodium recovery of 88 percent (76%+12% from wash).

EXAMPLE 37

Example 1 was repeated except the 0.63 mmol of pyridine was omitted and the reaction pressure was raised to 17,500 psia. Analysis of the reaction product showed 8.4 grams of ethylene glycol, 3.7 grams of methanol, 0.9 grams of water, 0.6 grams of methyl formate, 0.3 grams of propylene glycol, 0.4 grams of ethylene glycol monoformate, 1.3 grams of glycerine and a rhodium recovery of 95 percent (88%+7% from wash).

EXAMPLE 38

Example 1 was repeated except 0.65 mmol of ammonium benzoate was used in place of the pyridine. Analysis of the reaction product showed 6.2 grams of ethylene glycol, 3.0 grams of methanol and a rhodium recovery of 87 percent (81%+6% from wash).

EXAMPLE 39

Example 38 was repeated except 0.75 mmol of ammonium benzoate was charged to the reactor. Analysis of the reaction product showed 5.2 grams of ethylene glycol, 2.4 grams of methanol and a rhodium recovery of 83 percent (78%+5% from wash).

EXAMPLE 40

Example 39 was repeated except the 0.85 mmol of ammonium benzoate was charged to the reactor. Analysis of the reaction showed 5.4 grams of ethylene glycol, 2.7 grams of methanol and a rhodium recovery of 90 percent (84%+6% from wash).

EXAMPLE 41

Example 40 was repeated except 0.65 mmol of ammonium acetate was used in place of the ammonium benzoate. Analysis of the reaction product showed 6.1 grams of ethylene glycol, 2.8 grams of methanol and a rhodium recovery of 88 percent (80%+8% from wash).

EXAMPLE 42

Example 41 was repeated except 0.80 mmol of ammonium acetate was charged to the reactor. Analysis of the reaction product showed 7.1 grams of ethylene glycol, 3.4 grams of methanol and a rhodium recovery of 91 percent (83%+8% from wash).

EXAMPLE 43

Example 1 was repeated except 2.50 mmol of triisopropanolamine borate were used in place of the pyridine. Analysis of the reaction product showed 5.3 grams of ethylene glycol, 3.3 grams of methanol and a rhodium recovery of 67 percent (62%+5% from wash).

EXAMPLE 44

Example 43 was repeated except that 0.50 mmol of cesium formate in addition to the triisopropanolamine borate was charged to the reactor. Analysis of the reaction product showed 5.6 grams of ethylene glycol, 4.2 grams of methanol and a rhodium recovery of 80 percent (77%+3% from wash).

EXAMPLE 45

Example 44 was repeated except that 0.65 mmol of cesium formate was used in addition to the borate. Analysis of the reaction product showed 6.1 grams of ethylene glycol, 4.4 grams of methanol and a rhodium recovery of 88 percent (84%+4% from wash).

EXAMPLE 46

Example 45 was repeated except that 0.875 mmol of cesium formate was used in addition to the borate. Analysis of the reaction product showed 5.6 grams of ethylene glycol, 4.3 grams of methanol and a rhodium recovery of 83 percent (79%+4% from wash).

EXAMPLE 47

Example 1 was repeated except 0.65 mmol of cesium para-methylsulfonylbenzoate, $CH_3SO_2C_6H_4COOCs$, was used in place of the pyridine. Analysis of the reaction product showed 5.3 grams of ethylene glycol, 2.5 grams of methanol and a rhodium recovery of 88 percent (83%+5% from wash).

EXAMPLE 48

Example 47 was repeated except 0.85 mmol of cesium para-methylsulfonylbenzoate was used. Analysis of the reaction product showed 6.2 grams of ethylene glycol, 2.9 grams of methanol and a rhodium recovery of 87 percent (81%+6% from wash).

EXAMPLE 49

Example 48 was repeated except that 1.0 mmol of cesium para-methylsulfonylbenzoate was used. Analysis of the reaction product showed 5.9 grams of ethylene glycol, 3.4 grams of methanol and a rhodium recovery of 96 percent (87%+9% from wash).

What is claimed is:

1. The process of making alkane diols and triols having from 2 to 3 carbon atoms in the molecule which comprises reacting a mixture consisting essentially of oxides of carbon and hydrogen in the presence of a rhodium carbonyl complex and dimethylsulfone or a tetramethylene sulfone solvent at a pressure of from about 1000 psia. to about 50,000 psia. correlated with a temperature of about 100° C. to about 375° C. sufficient to produce said diols and triols.

2. The process of claim 1 wherein the pressure is from about 12,000 psia. to about 50,000 psia.

3. The process of claim 2 wherein the temperature is from about 150° C. to about 300° C.

4. The process of claim 3 wherein the temperature is from about 190° C. to about 275° C.

5. The process of claim 4 wherein the solvent is a tetramethylene sulfone.

6. The process of claim 5 wherein the solvent is sulfolane.

7. The process of claim 5 wherein the solvent is 3,4-bis(2-methoxyethoxy)sulfolane.

8. The process of claim 5 wherein the reaction is effected in the presence of at least one of a Lewis base nitrogen compound or a salt.

9. The process of claim 8 wherein the salt is present in the reaction in amounts of from about 0.5 mole to about 2.0 moles of salt for every six atoms of rhodium present in the reaction mixture.

10. The process of claim 9 wherein the salt is at least one selected from the group of Group I metal, Group II metal, ammonium, and bis(triorgano phosphine)iminium salts.

11. The process of claim 10 wherein the salt is at least one of a Group I alkali metal hydroxide, halide, alkoxide and carboxylate salt.

12. The process of claim 11 wherein the salt is a carboxylate salt.

13. The process of claim 12 wherein the salt is a cesium carboxylate.

14. The process of claim 13 wherein the salt is cesium p-methylsulfonylbenzoate.

15. The process of claim 13 wherein the salt is cesium formate.

16. The process of claim 13 wherein the salt is cesium benzoate.

17. The process of claim 13 wherein the solvent is sulfolane.

18. The process of claim 9 wherein the salt is at least one of an ammonium halide, hydroxide, alkoxide and carboxylate salt.

19. The process of claim 18 wherein the salt is an ammonium salt.

20. The process of claim 19 wherein the salt is an ammonium carboxylate salt.

21. The process of claim 20 wherein the salt is ammonium acetate.

22. The process of claim 20 wherein the salt is ammonium benzoate.

23. The process of claim 8 wherein the Lewis base nitrogen compound is an amine.

24. The process of claim 23 wherein the amine is pyridine.

25. The process of claim 23 wherein the amine is N-methylmorpholine.

26. The process of claim 23 wherein the amine is bis(1,8)-dimethylaminonaphthalene.

27. The process of claim 23 wherein the amine is 1,4-diazabicyclo[2.2.2]octane.

28. The process of claim 1 wherein the pressure is from about 1000 psig to about 12,000 psig and there is provided to the reaction a salt or a Lewis base nitrogen compound or mixtures thereof.

29. The process of claim 28 wherein the temperature is from about 150° C. to about 300° C.

30. The process of claim 29 wherein the temperature is from about 190° C. to about 275° C.

31. The process of claim 30 wherein the solvent is a tetramethylene sulfone.

32. The process of claim 31 wherein the solvent is sulfolane.

33. The process of claim 31 wherein the solvent is 3,4-bis(2-methoxyethoxy)sulfolane.

34. The process of claim 31 wherein the reaction is effected in the presence of at least one of a Lewis base nitrogen compound or a salt.

35. The process of claim 34 wherein the salt is present in the reaction in amounts of from about 0.5 mole to about 2.0 moles of salt for every six atoms of rhodium present in the reaction mixture.

36. The process of claim 35 wherein the salt is at least one selected from the group of Group I metal, Group II metal, ammonium, and bis(triorgano phosphine)iminium salts.

37. The process of claim 36 wherein the salt is at least one of a Group I alkali metal hydroxide, halide, alkoxide and carboxylate salt.

38. The process of claim 37 wherein the salt is a carboxylate salt.

39. The process of claim 38 wherein the salt is a cesium carboxylate.

40. The process of claim 39 wherein the salt is cesium p-methylsulfonylbenzoate.

41. The process of claim 39 wherein the salt is cesium formate.

42. The process of claim 39 wherein the salt is cesium benzoate.

43. The process of claim 39 wherein the solvent is sulfolane.

44. The process of claim 35 wherein the salt is at least one of an ammonium halide, hydroxide, alkoxide and carboxylate salt.

45. The process of claim 44 wherein the salt is an ammonium salt.

46. The process of claim 45 wherein the salt is an ammonium carboxylate salt.

47. The process of claim 46 wherein the salt is ammonium acetate.

48. The process of claim 43 wherein the salt is ammonium benzoate.

49. The process of claim 34 wherein the Lewis base nitrogen compound is an amine.

50. The process of claim 49 wherein the amine is pyridine.

51. The process of claim 49 wherein the amine is N-methylmorpholine.

52. The process of claim 49 wherein the amine is bis-(1,8)-dimethylaminonaphthalene.

53. The process of claim 49 wherein the amine is 1,4-diazabicyclo[2.2.2]octane.

54. The process of claim 49 wherein the tetramethylene sulfone is sulfolane.

* * * * *

UNITED STATES PATENT AND TRADEMARK OFFICE
CERTIFICATE OF CORRECTION

PATENT NO. : 4,224,237
DATED : Sept. 23, 1980
INVENTOR(S) : Leonard Kaplan

It is certified that error appears in the above—identified patent and that said Letters Patent is hereby corrected as shown below:

Column 13, line 6, "tri(hexane-2,4-dionato)" should read -- tris(hexane-2,4-dionato) -- .

Column 16, line 39, "10,0000" should read -- 10,000 -- .

Signed and Sealed this

Fourteenth Day of July 1981

[SEAL]

Attest:

Attesting Officer

GERALD J. MOSSINGHOFF

Commissioner of Patents and Trademarks